US008647855B2

(12) United States Patent
Taron et al.

(10) Patent No.: US 8,647,855 B2
(45) Date of Patent: Feb. 11, 2014

(54) GENETICALLY ENGINEERED YEAST FOR THE PRODUCTION OF BIOFUELS

(75) Inventors: Christopher H. Taron, Essex, MA (US); Paul A. Colussi, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 35 days.

(21) Appl. No.: 13/129,482

(22) PCT Filed: Nov. 16, 2009

(86) PCT No.: PCT/US2009/064511
§ 371 (c)(1),
(2), (4) Date: Jun. 7, 2011

(87) PCT Pub. No.: WO2010/059539
PCT Pub. Date: May 27, 2010

(65) Prior Publication Data
US 2011/0269202 A1    Nov. 3, 2011

Related U.S. Application Data

(60) Provisional application No. 61/116,440, filed on Nov. 20, 2008.

(51) Int. Cl.
| | | |
|---|---|---|
| C12N 1/00 | (2006.01) | |
| C12P 7/06 | (2006.01) | |
| C12N 9/00 | (2006.01) | |
| C07H 21/04 | (2006.01) | |

(52) U.S. Cl.
USPC ........ 435/254.2; 435/161; 435/183; 536/23.2

(58) Field of Classification Search
None
See application file for complete search history.

(56) References Cited

U.S. PATENT DOCUMENTS

| | | |
|---|---|---|
| 4,368,268 A | 1/1983 | Gong |
| 4,511,656 A | 4/1985 | Gong |
| 4,663,284 A | 5/1987 | Jeffries |
| 5,789,210 A | 8/1998 | Ho et al. |
| 5,866,382 A | 2/1999 | Hallborn et al. |
| 6,071,729 A | 6/2000 | Jeffries et al. |
| 6,582,944 B1 | 6/2003 | Hallborn et al. |
| 7,226,735 B2 | 6/2007 | Jeffries et al. |
| 7,285,403 B2 | 10/2007 | Jeffries et al. |

FOREIGN PATENT DOCUMENTS

EP     1499708 A1    1/2005

OTHER PUBLICATIONS

Shahidi et al. Trends in Food Science & Technology (1999), 10: 37-51.).*
Hill et al. Proc. Nat. Acad. Sci. USA 103:11206-11210 (2006).
Maullu et al., Appl Environ Microbiol 65(6):2745-7 (1999).
Fonseca et al., Appl Microbiol Biotechnol. 79(3):339-54 (2008).
Ikeda et al., 5 Bioresour Technol 97(8):1030-5 (2006).
Rattanakit et al., J Biosci Bioeng. 93(6):550-6 (2002).
Rattanakit et al., J Biosci Bioeng 95(4):391-396 (2003).
Vaughan-Martini & Martini, The Yeasts, A Taxonomic Study, C.P. Kurzman & J.W. Feld, Ed. Elsevier, New York, pp. 358-371 (1998).
Lachance, M.A., The Yeasts, A Taxonomic Study, C.P. Kurzman & J.W. Feld, Ed. Elsevier, New York, pp. 227-247 (1998).
Yamada-Okabe et al., Eur. J. Biochem. 268: 2498-2505 (2001).
Alvarez & Konopka Mol. Biol. Cell 18: 965-975 (2007).
Hinderlich et al. Eur. J. Biochem. 267:3301-3308 (2000).
Vincent et al. J. Biol. Chem. 279:2809-2816 (2004).
Shevchenko et al. Gene 216:31-38 (1998).
Colussi & Taron Appl. Environ. Microbiol. 71:7092-7098 (2005).
Sikorski & Heiter Genetics 122: 19-27 (1989).
Kurtzman, C.P. Pichia: E.C. Hansen emend. The Yeasts, A Taxonomic Study, C.P. Kurzman & J.W. Feld, Ed. Elsevier, New York, pp. 273-352 (1998).
Keyhani, N. & Roseman, S. Biochim et Biophys Acta, 1473, 108-122, 1999.
de Hoog, G.S.; Kurtzman, C.P.; Phaff, H.J.; & Miller, M.W. (1998) Ashbya: Eremothecium Borzi emend. C.P. Kurzman & J.W. Feld, Ed. The Yeasts: A Taxonomic Study (pp. 201-208) New York: Elsevier.
Meyer, R.W. Payne, D. (1998) Yarrow Candida Berkhout. C.P. Kurzman & J.W. Feld, Ed. The Yeasts: A Taxonomic Study (pp. 454-573) New York: Elsevier.
Lachance, M.A. & Phaff, H.J. (1998) Clavispora: Rodrigues de Miranda. C.P. Kurzman & J.W. Feld, Ed. The Yeasts: A Taxonomic Study (pp. 148-152) New York: Elsevier.
Nakase, T.; Suzuki, M.; Phaff, H.J. & Kurtzman, C.P. (1998) Debaryomyces: Lodder & Kreger-van Rij Nom. C.P. Kurzman & J.W. Feld, Ed. The Yeasts: A Taxonomic Study (pp. 157-173) New York: Elsevier.
Kurtzman, C.P. (1998) Lodderomyces: van der Walt C.P. Kurzman & J.W. Feld, Ed. The Yeasts: A Taxonomic Study (pp. 254-255) New York: Elsevier.
Kurtzman, C.P. (1998) Yarrowia van der Walt & von Arx. C.P. Kurzman & J.W. Feld, Ed. The Yeasts: A Taxonomic Study (pp. 420-421) New York: Elsevier.
Wendland etal App Env Microbiol 75 18 5840-5845 2009.

* cited by examiner

*Primary Examiner* — Iqbal H Chowdhury
(74) *Attorney, Agent, or Firm* — New England Biolabs, Inc; Harriet M. Strimpel

(57) ABSTRACT

Compositions and methods are provided for generating biofuels by fermentation from carbon sources other than glucose using genetically engineered yeast strains. For example, a *Saccharomyces* strain which is capable of converting glucose to ethanol but not of metabolizing N-acetyl glucosamine is genetically engineered to utilize N-acetyl glucosamine as a nutrient carbon source.

16 Claims, 10 Drawing Sheets

FIGURE 2

| Organism | Strain | UDP-GlcNAc Synthesis Proteins ||||
|---|---|---|---|---|---|
| | | Gfa1p | Gna1p | Pcm1p | Qri1p |
| Ashbya gossypii | ATCC 10895 | NP_982911 | NP_986057 | NP_983418 | NP_985358 |
| Candida albicans | SC5314 | XP_721697 | XP_721083 | XP_722331 | XP_720701 |
| Candida albicans | WO-1 | AAFO01000023 | AAFO01000053 | AAFO01000001 | AAFO01000058 |
| Candida glabrata | CBS 138 | XP_448593 | XP_445508 | XP_445128 | XP_449098 |
| Candida tropicalis | MYA-3404 | AAFN01000095 | AAFN01000046 | AAFN01000138 | AAFN01000005 |
| Clavispora lusitaniae | ATCC 42720 | AAFT01000073 | AAFT01000073 | AAFT01000001 | AAFT01000026 |
| Debaryomyces hansenii | CBS767 | XP_461639 | XP_457185 | XP_001525615 | XP_462598 |
| Kluyveromyces lactis | NRRL Y-1140 | XP_455692 | XP_453406 | XP_453110 | XP_454023 |
| Kluyveromyces waltii | NCYC 2644 | AADM01000093 | AADM01000144 | AADM01000266 | AADM01000007 |
| Lodderomyces elongisporus | NRRL YB-4239 | XP_001526195 | XP_001528746 | XP_458682 | XP_001525119 |
| Pichia guilliermondii | ATCC 6260 | XP_001487294 | XP_001487456 | XP_001483045 | XP_001487697 |
| Pichia stipitis | CBS 6054 | XP_001384265 | XP_001383463 | XP_001386954 | XP_001385188 |
| Saccharomyces bayanus | 623-6C | AAO32393 | AACG02000045 | AACG02000007 | AACG02000255 |
| Saccharomyces bayanus | MYC 623 | AACA01000032 | AACA01000011 | AACA01000046 | AACA01000623 |
| Saccahromyces castellii | NRRL Y-12630 | AAO32496 | AACF01000015 | AACF01000067 | AACF01000091 |
| Saccharomyces cerevisiae | S288C | NP_012818 | NP_116637 | NP_010856 | NP_010180 |
| Saccharomyces cerevisiae | RM11-1a | EDV11579 | EDV09823 | EDV08776 | EDV08373 |
| Saccharomyces cerevisiae | YJM789 | EDN64472 | EDN59133 | EDN62913 | EDN60256 |
| Saccharomyces kluyveri | CBS3082 | AAO32566 | AACE03000007 | AACE03000003 | AACE03000003 |
| Saccharomyces kudriavzevii | IFO 1802 | AACI02000058 | AACI02000531 | AACI02000117 | AACI02000697 |
| Saccharomyces mikatae | IFO 1815 | AABZ01000758 | AABZ01000094 | AABZ01000047 | AABZ01000241 |
| Saccharomyces paradoxus | NRRL Y-17217 | AABY01000026 | AABY01000015 | AABY01000108 | AABY01000084 |
| Vanderwaltozyma polyspora | DSM 70294 | XP_001642942 | XP_001643198 | XP_001646268 | XP_001645684 |
| Yarrowia lipolytica | CLIB122 | XP_501181 | XP_503060 | XP_504558 | XP_503486 |

FIGURE 5

| Organism | Strain | GlcNAc Metabolism Enzymes | | | GlcNAc Assimilation[1] |
|---|---|---|---|---|---|
| | | Nag5p | Nag2p | Nag1p | |
| Ashbya gossypii | ATCC 10895 | - | - | - | - |
| Candida albicans | SC5314 | XP_712286 | XP_712289 | XP_712288 | + |
| Candida albicans | WO-1 | AAFO01000061 | AAFO01000061 | AAFO01000061 | + |
| Candida glabrata | CBS 138 | - | - | - | - |
| Candida tropicalis | MYA-3404 | AAFN01000138 | AAFN01000138 | AAFN01000138 | + |
| Clavispora lusitaniae | ATCC 42720 | AAFT01000077 | AAFT01000076 | AAFT01000076 | + |
| Debaryomyces hansenii | CBS767 | XP_461411 | XP_461409 | XP_461410 | + |
| Kluyveromyces lactis | NRRL Y-1140 | - | - | - | - |
| Kluyveromyces waltii | NCYC 2644 | - | - | - | - |
| Lodderomyces elongisporus | NRRL YB-4239 | XP_001525748 | XP_001525746 | XP_001525747 | + |
| Pichia guilliermondii | ATCC 6260 | XP_001487103 | XP_001487101 | XP_001487102 | + |
| Pichia stipitis | CBS 6054 | XP_001385689 | XP_001385688 | XP_001385338 | + |
| Saccharomyces bayanus | 623-6C | - | - | - | - |
| Saccharomyces bayanus | MYC 623 | - | - | - | - |
| Saccharomyces castellii | NRRL Y-12630 | - | - | - | - |
| Saccharomyces cerevisiae | S288C | - | - | - | - |
| Saccharomyces cerevisiae | RM11-1a | - | - | - | - |
| Saccharomyces cerevisiae | YJM789 | - | - | - | - |
| Saccharomyces kluyveri | CBS3082 | - | - | - | - |
| Saccharomyces kudriavzevii | IFO 1802 | - | - | - | - |
| Saccharomyces mikatae | IFO 1815 | - | - | - | - |
| Saccharomyces paradoxus | NRRL Y-17217 | - | - | - | - |
| Vanderwaltozyma polyspora | DSM 70294 | - | - | - | - |
| Yarrowia lipolytica | CLIB122 | XP_504178 | XP_504176 | XP_501330 | + |

[1]GlcNAc assimilation phenotypes as reported in *The Yeasts, A Taxonomic Study*, C.P. Kurzman & J.W. Feld, Ed. Elsevier, New York, 1998

GENETICALLY ENGINEERED YEAST FOR THE PRODUCTION OF BIOFUELS

CROSS REFERENCE

This application is a §371 application of international application number PCT/US09/64511 filed on Nov. 16, 2009, which claims priority from U.S. provisional application No. 61/116,440 filed on Nov. 20, 2008, herein incorporated by reference.

BACKGROUND OF THE INVENTION

In recent years, rising fuel prices, concerns about greenhouse gas emissions and political instability in oil-producing regions have generated an increase in the interest of producing fuels from renewable biomass resources ("biofuels"). At the forefront of this effort has been a surge in the production of bioethanol. In a typical bioethanol production strategy, biomass is processed to release sugars that are then fed to microorganisms that ferment the sugars to ethanol. While both bacteria and yeasts are capable of ethanol production, the workhorse of industrial ethanol production to date has been yeast from the genus Saccharomyces, especially Saccharomyces cerevisiae (S. cerevisiae).

Processes have been described in which ethanol has been produced from simple sugars released from sugar cane and sugar beets, from starches isolated from corn and from sugars liberated from plant-derived cellulose (termed "cellulosic ethanol"). The latter typically involves the use of S. cerevisiae strains that have been genetically engineered to ferment pentose (5-carbon) sugars such as xylose (U.S. Pat. Nos. 4,368,268, 4,511,656, 4,663,284, 5,789,210, 5,866,382, 6,071,729, 6,582,944, 7,226,735, and 7,285,403) and arabinose (European Patent No. EP 1499708) in addition to glucose. While these processes are all viable, each also has drawbacks. Sugar cane, sugar beets and corn are natural resources that are also in the human food chain. Utilization of these resources for bioethanol generation has negatively impacted food prices. Additionally, each of the current methods employs large-scale exploitation of agricultural resources to generate the biomass needed for ethanol production. Thus, ethanol manufacturing is currently limited to geographic regions that are optimal for growth of energy crops. In one 2005 estimation, devoting all current U.S. corn production to generation of bioethanol would only offset U.S. petroleum use by 12% (Hill et al., Proc. Nat. Acad. Sci. USA 103:11206-11210 (2006)). Thus, to augment the current strategies for ethanol production, other types of sugar-rich biomass need to be considered for conversion to biofuels such as ethanol.

Chitin is generally regarded as the second most abundant polysaccharide in nature after cellulose. It is an unbranched β1,4-linked polymer of N-acetylglucosamine (GlcNAc) that is structurally quite similar to cellulose. It is a major component of insect exoskeletons, the shells of invertebrate crustaceans and cell walls of yeast and filamentous fungi. It has been estimated that >$10^{11}$ tons of chitin are produced annually in the biosphere. In marine waters, the annual chitin production from a single genus of zooplankton (copepods) is estimated to exceed billions of tons (Keyhani & Roseman, Biochimica et Biophysica Acta 1473: 108-122 (1999)). Additionally, hundreds of thousands of metric tons of chitin-containing shellfish waste are generated as a byproduct of the shrimp and crab industries annually, much of which is dumped back into the ocean for disposal or used for fertilizer. Finally, chitin is a significant component of fungal cell walls along with polymers of other fermentable sugars such as mannose (mannan) and glucose (glucan). Large amounts of fungal biomass are generated in various industrial processes for production of commercially important metabolites, industrial enzymes, and protein therapeutics, as well as brewing processes and even ethanol production. Additionally, fungi can be propagated on industrial waste products such as cheese whey (Maullu et al., Appl. Environ. Microbiol. 65(6):2745-7 (1999); Fonseca et al., Appl. Microbiol. Biotechnol. 79(3): 339-54 (2008), waste office paper (Ikeda et al., Bioresource Technol. 97(8):1030-5 (2006) and shellfish waste (Rattanakit et al., J. Bioscience and Bioeng. 93(6):550-6 (2002); Rattanakit et al., J. Bioscience and Bioeng. 95(4):391-396 (2003)). Thus, chitin is an abundant renewable source of sugars that can be considered in biofuel production strategies. However, despite its abundance, a significant drawback to its metabolic conversion to ethanol is the inability of various ethanol producing yeasts, especially yeast of the genus Saccharomyces, to metabolize and ferment the monomeric saccharide of chitin, the amino-sugar GlcNAc.

SUMMARY

In embodiments of the invention, a composition is provided that includes a genetically engineered yeast cell such as Saccharomyces containing a heterologous DNA encoding at least one protein required for GlcNAc metabolism such that the yeast host cell in the absence of the heterologous DNA is not capable of growth on a nutrient medium in which the carbon source is GlcNAc, the genetically modified yeast being capable of growing on a medium wherein the carbon source is GlcNAc. Preferably, the composition should be capable of converting GlcNAc to ethanol. This may be achieved where the at least one protein required for GlcNAc metabolism is selected from the group consisting of GlcNAc kinase, N-acetylglucosamine-6-phosphate (GlcNAc6P) deacetylase and glucosamine-6-phosphate (Glc6P) deaminase. Additionally, the at least one protein may be selected from the group consisting of Candida albicans (C. albicans or Ca) proteins (p) CaNgt1p, CaNag5p, CaNag2p and CaNag1p.

In another embodiment of the invention, a method is provided for making a biofuel such as ethanol which includes the steps of: modifying a yeast strain such as Saccharomyces that naturally does not metabolize GlcNAc by introducing DNA encoding at least one protein required for GlcNAc metabolism optionally derived from C. albicans; providing GlcNAc as a source of carbon to the nutrient medium for growing the modified yeast strain; and permitting the growth of the yeast strain by metabolism of GlcNAc. The above method may further include propagating the yeast strain under oxygenation conditions that result in the production of ethanol such as an aerobic, oxygen-limited or anaerobic environment or in both anaerobic and aerobic environments during different phases of fermentation. Embodiments of the method may further include forming a heterologous DNA by assembling gene expression cassettes using genes such as those derived from C. albicans in a two-stage PCR reaction for modifying the Saccharomyces host cell.

In the method, the at least one protein required for GlcNAc metabolism may be selected from the group consisting of GlcNac kinase, GlcNac6P deacetylase, and Glc6P deaminase or from the group consisting of CaNgt1p, CaNag5p, CaNag2p and CaNag1p for making the biofuel The yeast strain may be propagated in a growth medium that contains at least one other sugar in addition to GlcNAc, for example, glucose, mannose, galactose, arabinose, fructose, xylose or glucosamine. The GlcNAc may be obtained as a degradation product from chitin.

BRIEF DESCRIPTION OF THE DRAWINGS

FIG. 2 is a table showing the presence of UDP-GlcNAc synthesis enzymes encoded by the sequenced genomes of ascomycete yeasts. Orthologs of enzymes involved in UDP-GlcNAc synthesis are invariably conserved in each organism. Genes encoding these proteins were identified by searching GenBank sequences using the algorithms blastp and tblastn and S. cerevisaie Gfa1p, Gna1p, Pcm1p and Qri1p sequences as search queries. Displayed GenBank accession numbers refer either to homologous protein sequences (for fully annotated genomes) or DNA sequences encoding an open reading frame (ORF) with high homology to the query sequence (for genomes where protein annotation has not yet been completed).

FIG. 5 is a table showing the presence of GlcNAc metabolic enzymes encoded by the sequenced genomes of ascomycete yeasts. C. albicans GlcNAc processing enzymes Nag5p, Nag2p and Nag1p were used as query sequences for identification of orthologous proteins in GenBank databases using the programs blastp and tblastn. Displayed GenBank accession numbers refer either to homologous protein sequences (for fully annotated genomes) or DNA sequences encoding an ORF with high homology to the query sequence (for genomes where protein annotation has not yet been completed). Notably, yeasts of the genus Saccharomyces and Kluyveromyces, and the organisms Ashbya gossypii, Candida glabrata, and Vanderwaltozyma polyspora lack the enzymes needed to facilitate entry of GlcNAc into central metabolism. Correspondingly, each of these organisms showed an inability to assimilate GlcNAc (The Yeasts, A Taxonomic Study, C. P. Kurzman & J. W. Feld, Ed. Elsevier, New York, 1998, pp. 148-152; 157-173; 201-208; 227-247; 254-255; 273-352; 358-371; 420-421; 454-573).

In FIG. 10A, PCR is used to amplify a fragment of the S. cerevisiae PGK promoter and to introduce an ~100 bp piece of DNA homologous to the first 100 bp of the C. albicans gene of interest (white box). Additionally, the target C. albicans gene of interest (C.a. GOI) is amplified from the C. albicans chromosome and an ~100 bp piece of DNA homologous to the 3' end of the PGK promoter is introduced (black box). In FIG. 10B, a second round of PCR is used to "knit" the two fragments together. In this reaction, the regions of overlapping homology on the two template fragments anneal and are extended by the polymerase to create a small amount of a fused template having the C.a. GOI immediately downstream of the promoter. This desired expression fragment is a target for primers that anneal to its extreme 5' and 3' ends and is further amplified by thermocycling. Following amplification, the fragment is cloned into an S. cerevisiae vector and introduced into yeast cells for expression of the C.a. GOI.

DETAILED DESCRIPTION OF EMBODIMENTS

Present embodiments of the invention relate to methods for generation of ethanol from the monomeric subunit of the biopolymer chitin (polymer of the aminosugar N-acetylglycosamine (GlcNAc)) using engineered yeast.

Figure 1:
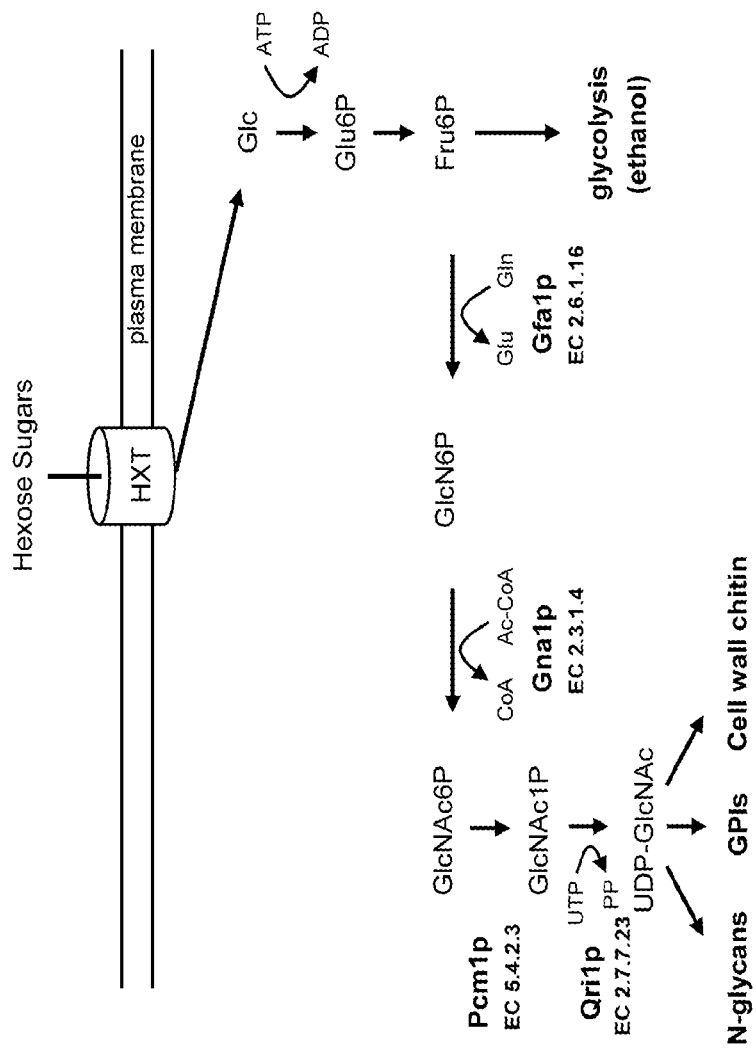
FIG. 1 is a schematic depicting entry of six-carbon sugars (hexoses) into yeast cells and their bioconversion to uridine diphosphate-GlcNAc (UDP-GlcNAc) or entry into glycolysis. Glucose is typically internalized via one or more hexose permeases and is converted to fructose-6-phosphate (Fru6P), which can either continue into glycolysis (general metabolism and ethanol production) or can be bioconverted into UDP-GlcNAc by the sequential action of glutamine-fructose-6-phosphate aminotransferase (Gfa1p; EC 2.6.2.16), GlcN-6-phosphate acetyltransferase (Gna1p; EC 2.3.1.4), GlcNAc-phosphate mutase (Pcm1p; EC 5.4.2.3) and UDP-GlcNAc pyrophosphorylase (Qri1p; EC 2.7.7.23). Abbreviations: HXT, hexose transporter; Glu6P, glucose-6-phosphate; GPIs, glycosylphosphatidylinositols.

All yeasts are capable of importing and metabolizing neutral hexose sugars such as glucose, mannose, and galactose. Importation of these sugars occurs via permeases integral to the plasma membrane. Imported sugars are processed to generate cellular energy for growth via glycolysis (FIG. 1). A metabolic byproduct of this pathway in some yeast types is ethanol which is typically formed when oxygen is limited or absent. However, not all yeasts share the same fermentative tendencies and produce or consume ethanol to different extents and under different conditions. For example, some yeasts, such as Saccharomyces species, metabolize sugars to ethanol without completely oxidizing them to $CO_2$, even in the presence of oxygen. These yeasts are termed "Crabtree-positive". Other yeasts, such as C. albicans, metabolize sugars to $CO_2$ in the presence of oxygen and accumulate little ethanol, and are termed "Crabtree-negative" yeasts. Yeasts of the Saccharomyces genus excel at ethanol generation for several reasons: they are fast growing; they efficiently both produce and consume ethanol under a wide range of oxygenation; and they are tolerant of high concentrations of ethanol.

Yeast cells produce the compound UDP-GlcNAc. This GlcNAc donor is utilized in several essential glycosylation pathways such as N-glycosylation, GPI-anchoring of proteins and chitin synthesis. The process of forming UDP-GlcNAc is highly conserved and is depicted by the pathway shown in FIG. 1. In this pathway, Fru6P is acted upon by enzymes that facilitate its sequential conversion to glucosamine-6-phosphate (GlcN6P, EC 2.6.1.16), GlcNAc6p (EC 2.3.1.4), GlcNAc1P (EC 5.4.2.3) and UDP-GlcNAc (EC 2.7.7.23). The four enzymes that comprise this pathway are highly conserved and genes encoding these enzymes are invariably found in the genomes of all sequenced ascomycete yeasts (FIG. 2).

Figure 3:
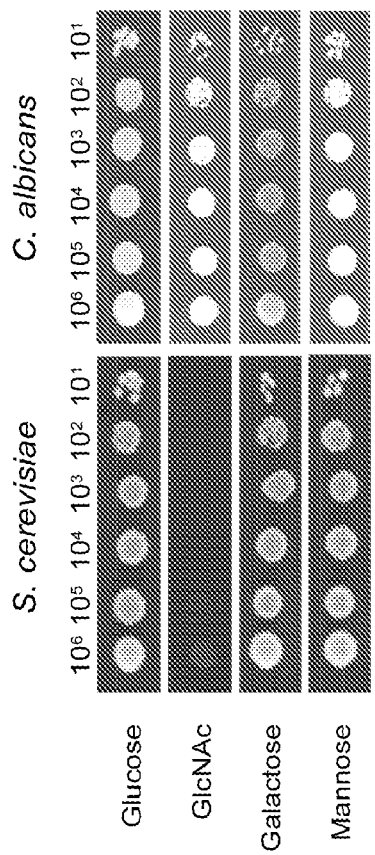
FIG. 3 shows growth of S. cerevisiae and C. albicans on yeast nitrogen base agar medium containing 100 mM glucose, 100 mM GlcNAc, 100 mM galactose or 100 mM mannose as the sole source of carbon. C. albicans is able to utilize all sugars for growth, whereas, S. cerevisae is unable to utilize GlcNAc as a carbon source and does not grow on that media. Cells were serially diluted and spotted onto the agar medium. Column headings indicate the total number of cells applied to the plate in each spot.

For a yeast cell to utilize GlcNAc as an exclusive source of cellular carbon, it is desirable that it be able to: (i) import GlcNAc; (ii) form UDP-GlcNAc to support essential glycosylation reactions; and (iii) convert the sugar into compounds that can enter the pathways of central metabolism (e.g., glycolysis). Not all yeasts share these abilities. We have shown directly that S. cerevisiae is not capable of GlcNAc assimilation, whereas C. albicans is (FIG. 3). Additionally, a published analysis of 14 known yeasts comprising the genus Saccharomyces (Vaughan-Martini & Martini, The Yeasts, A Taxonomic Study, Elsevier, New York, pp 358-371 (1998)), and 15 yeasts comprising the genus Kluyveromyces (Lachance, M. A., The Yeasts, A Taxonomic Study, Elsevier, New York, pp 227-247 (1998)), has shown that no members of either genus are capable of assimilating GlcNAc.

Figure 4:
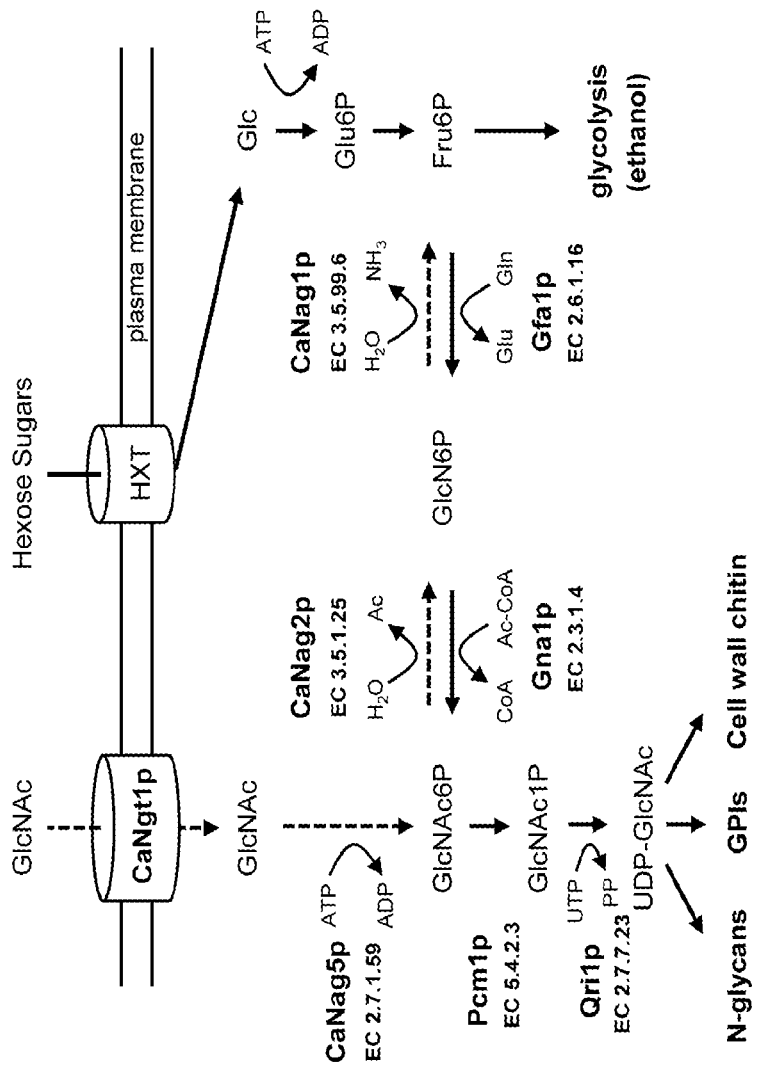
FIG. 4 is a schematic depicting C. albicans GlcNAc assimilation in relationship to glycolysis and UDP-GlcNAc formation. Shown in dotted lines is the C. albicans pathway for internalization of GlcNAc, its bioconversion to Fru6P and entry into general metabolism through the sequential action of the GlcNAc-specific transporter CaNgt1p, GlcNAc kinase (CaNag5p; EC 2.7.1.59), GlcNAc-6-phosphate deacetylase (CaNag2p; EC 3.5.1.25) and GlcN-6-phosphate deaminase (CaNag1p; EC 3.5.99.6). Abbreviations: ATP, adenosine triphosphate; ADP, adenosine diphosphate; UTP, uridine triphosphate; $PP_i$, inorganic phosphate; CoA, coenzyme A; Ac-CoA, acetyl coenzyme A; Glu, glutamic acid; Gln, glutamine.

In C. albicans, several proteins have been implicated in GlcNAc assimilation (Yamada-Okabe et al., Eur. J. Biochem. 268: 2498-2505 (2001)) and GlcNAc-specific import (Alvarez & Konopka Mol. Biol. Cell 18: 965-975 (2007)). The probable pathway for GlcNAc assimilation in C. albicans is shown in dotted lines in FIG. 4. In this scenario, GlcNAc is transported into the cytoplasm by the GlcNAc-specific membrane transporter CaNgt1p. Internalized GlcNAc is first phosphorylated by GlcNAc kinase (EC 2.7.1.59, CaNag5p) to form GlcNAc6P. GlcNAc6P deacetylase (EC 3.5.1.25, CaNag2p) then removes an acetyl group to form GlcN6P. Finally, GlcN6P deaminase (EC 3.5.99.6, CaNag1p) converts GlcN6P to ammonia and the glycolysis intermediate Fru6P. Analysis of 24 ascomycete yeast genomes present in the GenBank database at the time of this study indicates that not all yeasts carry genes encoding GlcNAc assimilation enzymes (FIG. 5). Of the organisms that do, all are also capable of GlcNAc assimilation. Notably, the sequenced genomes of several Saccharomyces and Kluyveromyces yeasts neither encoded GlcNAc assimilation enzymes nor were capable of GlcNAc assimilation (FIG. 5).

Figure 6:
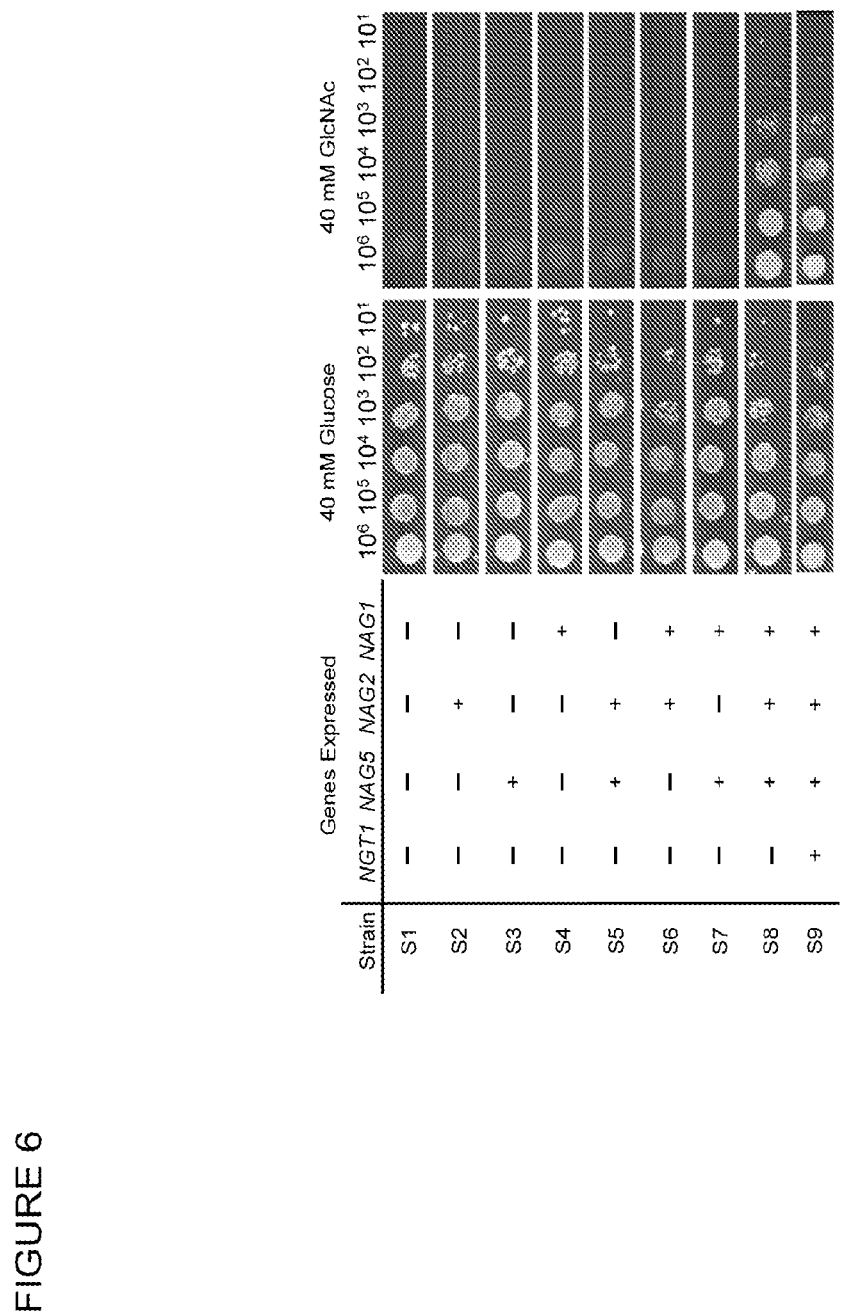
FIG. 6 shows the growth of S. cerevisiae cells expressing various combinations of GlcNAc metabolic enzymes from C. albicans on yeast nitrogen base medium supplemented with either 100 mM glucose or 100 mM GlcNAc as a carbon source. S1-S8 are S. cerevisiae strains harboring separate expression vectors that each produce a combination of CaNgt1p, CaNag5p, CaNag2p or CaNag1p. Cells from each strain were serially diluted and spotted onto the agar medium. Column headings indicate the total number of cells in each spot applied to the plate. Only S. cerevisiae strains S8 and S9 which each co-express CaNag5p, CaNag2p and CaNag1p, and optionally CaNgt1p (in the case of strain S9) were capable of growth on GlcNAc as a carbon source.
Figure 7:
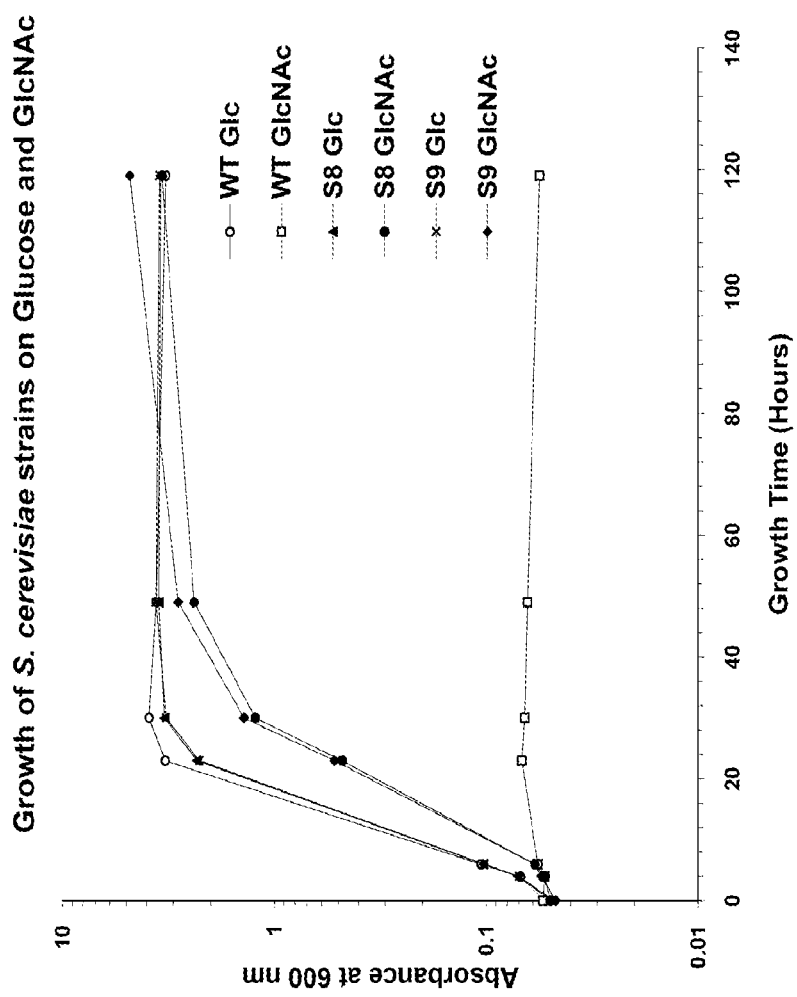
FIG. 7 shows growth curves of parental BY4734 S. cerevisiae cells (WT, ATCC 200896), S. cerevisiae strain S8 (which produces CaNag5p, CaNag2p and CaNag1p) and S. cerevisiae strain S9 (which produces CaNgt1p, CaNag5p, CaNag2p and CaNag1p) in yeast nitrogen base medium supplemented with either 100 mM glucose or 100 mM GlcNAc as a carbon source. WT cells are unable to grow in medium containing 100 mM GlcNAc. Strains S8 and S9 are fully capable of growth on GlcNAc despite showing a slight reduction in their rate of growth. Both strains reached maximal culture densities identical to those achieved when the strains (and the parental WT strain) were grown on glucose.

In an embodiment of the invention, S. cerevisiae strains capable of metabolizing GlcNAc were created by metabolically engineering a pathway that facilitates entry of internalized GlcNAc into glycolysis. Two S. cerevisiae strains were genetically engineered to simultaneously express C. albicans genes encoding the enzymes CaNag5p, CaNag2p, CaNag1p, optionally with (FIG. 6, strain S9) or without (FIG. 6, strain S8) coexpression of the C. albicans gene encoding CaNgt1p. Both strains S8 and S9 were capable of utilizing GlcNAc provided in the growth medium as a sole source of cellular carbon, indicating the engineered cells were capable of internalizing GlcNAc and allowing its entry into central metabolism. Strains S8 and S9 were healthy and grew to the same level of culture saturation as the parent strain (wild-type, WT) in either glucose- or GlcNAc-containing growth medium (FIG. 7). Expression of genes encoding these enzymes can be achieved using either heterologous or endogenous promoters incorporated in one or more centromeric or episomal expression vectors, or by integration of one or more of the expression vectors into the host chromosome using methods known in the art.

In another embodiment, a second possible route to direct GlcNAc into glycolysis involves direct deacetylation of internalized GlcNAc to GlcN by GlcNAc deacetylase. GlcN is then phosphorylated by hexokinase or glucokinase to form GlcN6P which is deaminated by GlcN6P deaminase to form Fru6P.

Figure 9:
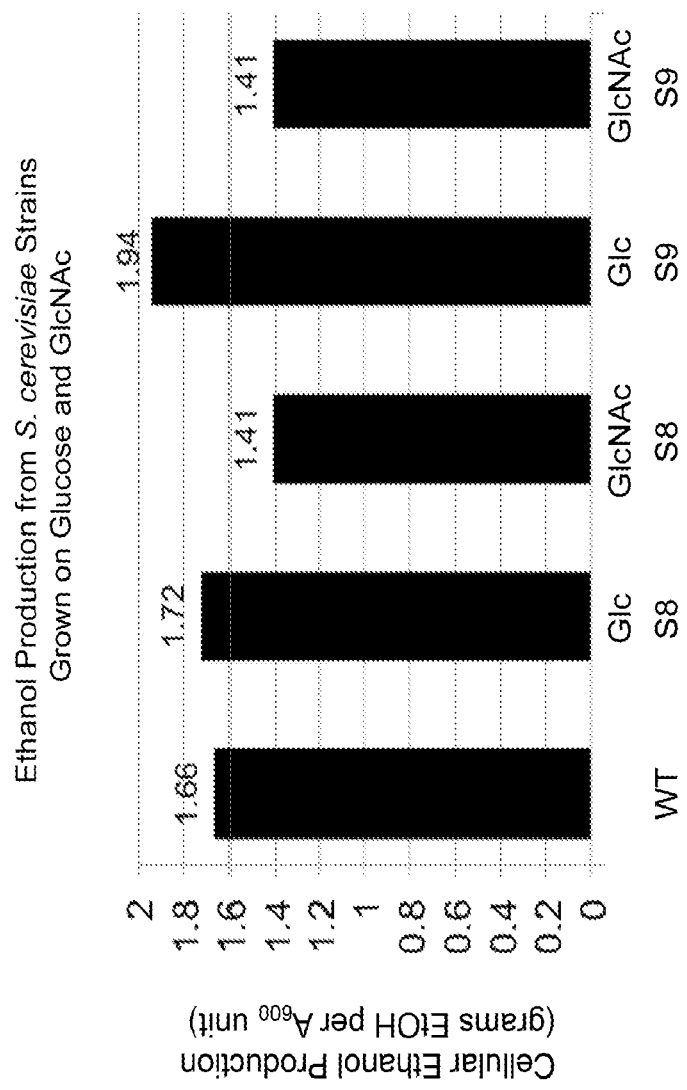
FIG. 9 depicts ethanol production in modified S. cerevisiae cells when fed 100 mM glucose or 100 mM GlcNAc in yeast nitrogen base medium and grown under oxygen-limiting conditions for 49 hours. Strains S8 and S9 yield 85% of the amount of ethanol produced by the parental strain (BY4734, WT) grown on glucose indicating that the engineered yeast strains are fully capable of fermenting GlcNAc.

In additional preferred embodiments, metabolically engineered S. cerevisiae strains S8 and S9 can be used to ferment GlcNAc provided in the growth medium to ethanol (FIG. 9). Ethanol can be produced from GlcNAc under aerobic or oxygen-limiting (semi-aerobic) or anaerobic culturing conditions. Uniform feed solutions of GlcNAc can be fed to cells for fermentation, or GlcNAc can be provided in mixtures with other sugars.

Where mixtures of nutrients are used in fermentation of the yeast to produce ethanol, GlcNAc can be combined with monosaccharides derived from carbohydrate polymers like glucose (from glucan or cellulose), GlcN (from chitin), or mannose (from mannan). Additionally, strains described in the art that ferment pentose (5-carbon) sugars such as xylose (U.S. Pat. Nos. 4,368,268, 4,511,656, 4,663,284, 5,789,210, 5,866,382, 6,071,729, 6,582,944, 7,226,735, and 7,285,403) and arabinose (European Patent No. EP 1499708) could be engineered using the present invention to also ferment GlcNAc by expressing GlcNAc metabolic genes. Thus, sugar mixtures can also include GlcNAc in combination with xylose, arabinose and fructose. In all cases, sugar mixtures can be presented to cells in any molar ratio of the individual monosaccharides.

Fermentation can be accomplished using batch, fed-batch, solid-state, or continuous-flow (chemostat) bioreactor cell cultivation methods known in the art.

All references cited herein, including U.S. provisional application No. 61/116,440 filed Nov. 20, 2008, are hereby incorporated by reference.

EXAMPLES

Example 1

Sugar Assimilation by S. cerevisiae and C. albicans

The ability of a comprehensive set of known yeast species to assimilate GlcNAc has previously been published (The Yeasts, A Taxonomic Study, C. P. Kurzman & J. W. Feld, Ed. Elsevier, New York, 1998). Here we illustrate the ability of C.

*albicans* and *S. cerevisiae* to assimilate glucose, galactose, mannose and GlcNAc.

Strains *C. albicans* CAI4 (ATCC MYA-682) and *S. cerevisiae* BY4734 (ATCC 200896) were streaked and grown on synthetic medium (Difco™ yeast nitrogen base medium (Beckton, Dickinson & Co, Sparks, Md.) supplemented with the necessary amino acids and nucleotides needed to complement strain auxotrophies, 100 mM of glucose and 2% (w/v) agar at 30° C. for 2 days. A small aliquot of cells from each streak was suspended in 0.25 mL liquid synthetic medium containing no supplements or glucose. One hundred microliters of each suspension was placed in a microtiter plate well and subjected to 10-fold serial dilutions with fresh synthetic medium. Samples (5 µL) of each dilution were spotted onto synthetic agar medium plates supplemented with the necessary amino acids and nucleotides needed to complement strain auxotrophies and 100 mM galactose, 100 mM glucose, 100 mM mannose or 100 mM GlcNAc. Plates were incubated for 4 days at 30° C. *C. albicans* CAI4 was able to assimilate all four sugars, whereas *S. cerevisiae* BY4734 was only capable of assimilating the neutral sugars mannose, glucose and galactose (FIG. 3). No growth of *S. cerevisiae* was observed on medium containing GlcNAc (FIG. 3).

Example 2

Assembly of Vectors for Expression of GlcNAc Metabolism Genes in *S. cerevisiae*

*S. cerevisiae* lacks GlcNAc kinase (EC 2.7.1.59), GlcNAc6P deacetylase (EC 3.5.1.25) and GlcN6P deaminase (EC 3.5.99.6) enzyme activities (FIG. 5) and does not assimilate GlcNAc. We sought to determine if expression of genes encoding these enzymes confers upon *S. cerevisiae* the ability to assimilate GlcNAc. Genes encoding GlcNAc kinase (Hinderlich et al., *Eur. J. Biochem.* 267:3301-3308 (2000)), GlcNAc6P deacetylase (Vincent et al., *J. Biol. Chem.* 279: 2809-2816 (2004)) and GlcN6P deaminase (Shevchenko et al., *Gene* 216:31-38 (1998)) proteins have been characterized and cloned from various organisms. Each of these protein families is highly conserved. We elected to use the *C. albicans* genes encoding these enzymes for this experimentation; however, genes encoding these proteins from other organisms could also be used. *C. albicans* genes CaNAG5, CaNAG2 and CaNAG1 were cloned and expressed in *S. cerevisiae*. In addition, the *C. albicans* NGT1 gene encoding a GlcNAc-specific permease was cloned for expression in *S. cerevisiae*.

Figure 10:
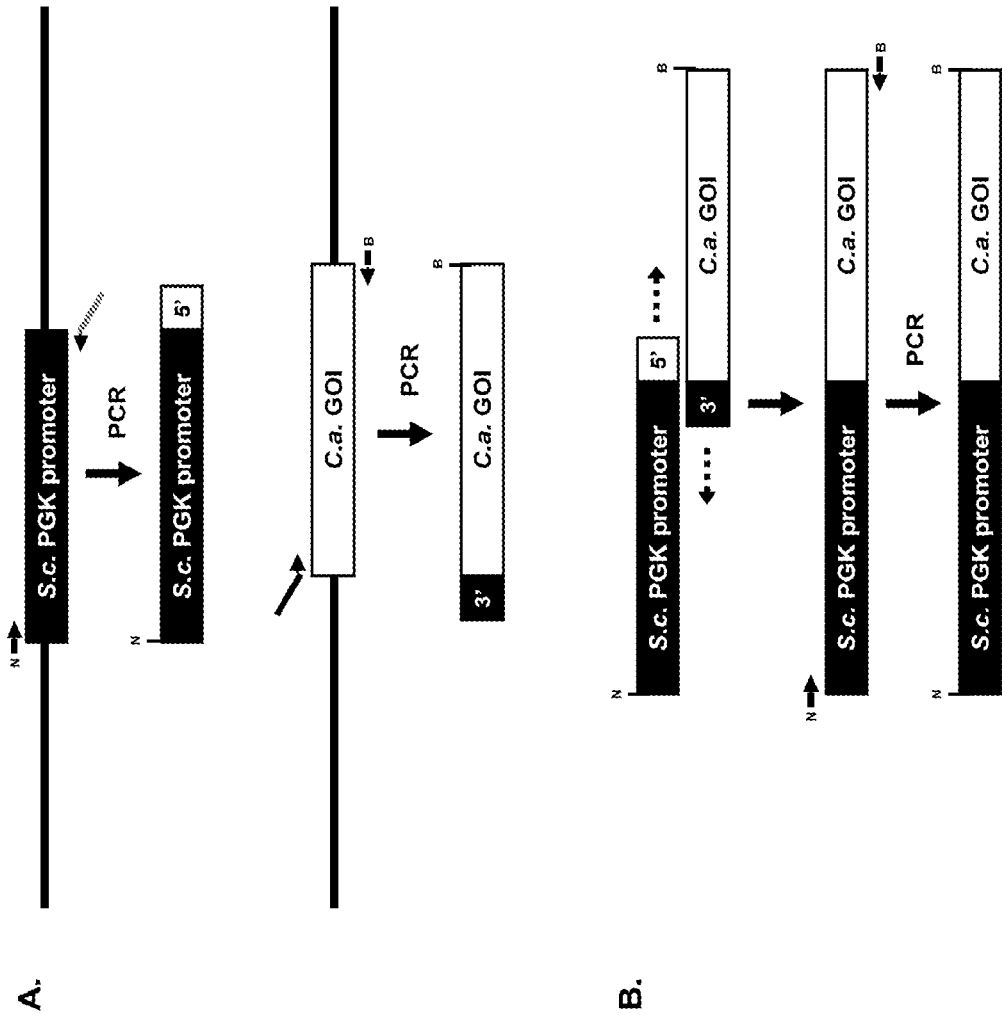
FIGS. 10A and 10B depict the method used for assembly of yeast gene expression cassettes using "PCR knitting".

GlcNAc metabolism genes were cloned and placed downstream of the *S. cerevisiae* anti-3-phosphoglycerate kinase (PGK) promoter using a two-stage "PCR-knitting" method (FIG. 10). In the first stage, each gene was amplified from *C. albicans* genomic DNA in a manner that introduced the terminal ~100 bp of the *S. cerevisiae* PGK promoter to each gene's 5' end. Additionally, the *S. cerevisiae* PGK promoter was amplified from vector pGBN1$_{PGK}$ (Colussi & Taron *Appl. Environ. Microbiol.* 71:7092-7098 (2005)) in four separate reactions that each introduced DNA corresponding to the first ~100 bp of CaNAG5, CaNAG2, CaNAG1 or CaNGT1 to the promoter's 3' end (FIG. 10A). In the second stage of expression fragment assembly, each amplified *C. albicans* gene was fused to its corresponding PGK promoter fragment using a second round of PCR (FIG. 10B). In this reaction, overlapping regions of homologous DNA present on amplified genes and promoter fragments anneal and extend to create a small amount of full-length template fragment, which is then amplified for cloning. The resulting amplified DNA fragments contain the PGK promoter upstream of the desired gene and were cloned into the NotI-BamHI sites of individual pRS400-series vectors (Sikorski & Heiter Genetics 122: 19-27 (1989); ATCC 87538) for introduction into *S. cerevisiae*.

For the first round PCRs (FIG. 10A), specific primer pairs used in the amplification of each gene were as follows:

CaNAG5 was amplified with the forward primer
NAG5-FP
                                         (SEQ ID NO: 1)
5'-TTATCTACTTTTTACAACAAATATAAAACAATGACTGAGACTACAT
TAGTGGGTTGCGT-3'
and the reverse primer NAG5-RP
                                         (SEQ ID NO: 2)
5'-CGCGGATCCCTACTTATGATAGGCAGCACCTATGGC-3'.

CaNAG2 was amplified with the forward primer
NAG2-FP
                                         (SEQ ID NO: 3)
5'-TTATCTACTTTTTACAACAAATATAAAACAATGTCATTTACTAGAT
TCACAAACTGTCAT-3'
and the reverse primer NAG2-RP
                                         (SEQ ID NO: 4)
5'-CGCGGATCCCTATAAAACAGCAGTTAATTTATC-3'.

CaNAG1 was amplified with the forward primer
NAG1-FP
                                         (SEQ ID NO: 5)
5'-TTATCTACTTTTTACAACAAATATAAAACAATGAGACAAGCTATAT
TTTCCAACCCTAAC-3'
and the reverse primer NAG1-RP
                                         (SEQ ID NO: 6)
5'-CGCGGATCCCTACAACTTTGACTTTAATCCAGCGGC-3'.

CaNGT1 was amplified with the forward primer
NGT1-FP
                                         (SEQ ID NO: 7)
5'-TTATCTACTTTTTACAACAAATATAAAACAATGGAGAAAGATCAAA
CTAAAATGGATATT-3'
and the reverse primer NGT1-RP
                                         (SEQ ID NO: 8)
5'-CGCGGATCCTTACTCAATATGTACTGTTGTTGA-3'.

The PGK promoter was amplified with the forward
primer PGK-FP
                                         (SEQ ID NO: 9)
5'-ATAAGAATGCGGCGGCGTGGCCTCTTATCGAGAAAGAAAT-3'
and the reverse primers PGK-RP1
                                         (SEQ ID NO: 10)
5'-ACGCAACCCACTAATGCTAGTCTCAGTCATTGTTTTATATTTGTTG
TAAAAAGTAGATAA-3', PGK-RP2
                                         (SEQ ID NO: 11)
5'-ATGACAGTTTGTGAATCTAGTAAATGACATTGTTTTATATTTGTTG
TAAAAAGTAGATAA-3', PGK-RP3
                                         (SEQ ID NO: 12)
5'-GTTAGGGTTGGAAAATATAGCTTGTCTCATTGTTTTATATTTGTTG
TAAAAAGTAGATAA-3'
and PGK-RP4
                                         (SEQ ID NO: 13)
5'-AATATCCATTTTAGTTTGATCTTTCTCCATTGTTTTATATTTGTTG
TAAAAAGTAGATAA-3'
each having a tail homologous to CaNAG5,
CaNAG2, CaNAG1 or CaNGT1, respectively.

First round PCRs were performed using DeepVent™ (New England BioLabs, Ipswich, Mass.), Taq or Phusion® DNA polymerases (New England BioLabs, Ipswich, Mass.; trademark owned by Finnzymes, Espoo, Finland). For PCR using DeepVent™ or Taq, PCR mixtures contained 0.2 mM deoxynucleoside triphosphates, 0.5 µg of each primer, 1× Thermopol buffer (20 mM Tris, pH 8, 10 mM KCl, 10 mM $(NH_4)_2SO_4$, 2 mM $MgSO_4$, 0.1% Triton X-100), and 100 ng template DNA in a total reaction volume of 50 µl. Reactions with Phusion® DNA polymerase contained 0.2 mM deoxynucleoside triphosphates, 0.5 µg of each primer, 1× Phusion® HF Buffer (New England BioLabs, Ipswich, Mass.), and 100 ng template DNA in a total reaction volume of 50 µl. Thermocycling for reactions containing DeepVent™ or Taq DNA polymerases consisted of a "hot start" at 95° C. for 10 min, followed by 30 cycles of successive incubations at 94° C. for 30 s, 58° C. for 30 s, and 72° C. (1 min per kb of DNA). After thermocycling, a final extension was performed at 72° C. for 10 min. Thermocycling for reactions containing Phusion® DNA polymerase consisted of a "hot start" at 98° C. for 30 sec, followed by 30 cycles of successive incubations at 98° C. for 30 s, 58° C. for 30 s, and 72° C. (30 sec per kb of DNA). After thermocycling, a final extension was performed at 72° C. for 5 min.

Second round "knitting" PCRs were all performed using Phusion®DNA polymerase (FIG. 10B). Reactions conditions were as listed above for PCR with Phusion® with the exception that ~200 ng each of two different templates were present in each reaction (e.g. the CaNAG5 gene with a 5' tail homologous to the PGK promoter and the PGK promoter with a 3' tail homologous to the CaNAG5 gene [FIG. 10B]). Primer pairs used in "knitting" CaNAG5, CaNAG2, CaNAG1 and CaNGT1 to the PGK promoter were PGK forward primer/NAGS reverse primer; PGK forward primer/NAG2 reverse primer; PGK forward primer/NAG1 reverse primer; PGK forward primer/NGT1 reverse primer, respectively. Amplified products were digested with NotI and BamHI and ligated into the NotI-BamHI sites of pRS400-series vectors including pRS413, pRS414, pRS415 and pRS416 (ATCC 87538) using standard methods known in the art. Specifically, PGK-CaNAG5, PGK-CaNAG2, PGK-CaNAG1 and PGK-CaNGT1 fragments were cloned into the NotI-BamHI sites of the centromeric vectors, pRS415, pRS413, pRS416 and pRS414, respectively.

Example 3

Assimilation of GlcNAc by Engineered *S. cerevisiae* Strains

Expression vectors containing *C. albicans* GlcNAc metabolism genes assembled in Example 1 were introduced into *S. cerevisiae* BY4734 via transformation using lithium acetate, a method well-known in the art. *S. cerevisiae* strains containing all combinations of 1, 2 or 3 expression vectors (pRS415-CaNAG5, pRS413-CaNAG2 and pRS416-CaNAG1) were assembled to create strains S1 to S8. Additionally, pRS414-CaNGT1 was introduced into the S8 background to generate strain S9.

Strains S1-59 were tested for their ability to assimilate GlcNAc. Each strain was streaked and grown on synthetic agar medium containing 100 mM glucose (see Example 1) at 30° C. for 2 days. A small aliquot of cells from each streak was suspended in 0.25 mL liquid synthetic medium containing no supplements or glucose to a final concentration of $10^8$ cells $mL^{-1}$. One hundred microliters of each suspension was placed in a microtiter plate well and subjected to 10-fold serial dilutions with fresh synthetic medium. Samples (5 µL) of each dilution were spotted onto synthetic agar medium plates supplemented with the necessary amino acids and nucleotides needed to complement strain auxotrophies and either 100 mM glucose or 100 mM GlcNAc. Plates were incubated for 4 days at 30° C. Strain S8 co-expressing CaNAG5, CaNAG2 and CaNAG1 and strain S9, a derivative of strain S8 additionally co-expressing CaNGT1, were entirely capable of growth on medium containing GlcNAc as the sole carbon source (FIG. 6). Surprisingly, the survival of strain S8, which lacks a heterologous GlcNAc-specific permease, indicated that *S. cerevisiae* cells are innately capable of importing GlcNAc into the cytoplasm likely through the function endogenous hexose transporters, despite lacking enzymes that facilitate GlcNAc metabolism.

Example 4

GlcNAc Import into *S. cerevisiae* Cells

Control strain S1, and GlcNAc-assimilating strains S8 and S9 were cultured in yeast nitrogen base medium (Difco Laboratories, Detroit, Mich.) supplemented with 20 µg $mL^{-1}$ methionine and 2% (w/v) glucose with shaking at 30° C. Cells were harvested when the culture reached a cell density of approximately $5-10×10^6$ cells $mL^{-1}$. Harvested cells were washed twice with 10 mL of yeast synthetic medium lacking a carbon source (no carbon source [NCS] medium) and re-suspended in the NCS medium at a density of $1×10^8$ cells $mL^{-1}$. Five microliters (5 µCi) of [$^3$H]GlcNAc (30 Ci $mmol^{-1}$) were delivered to triplicate wells in a 96 well plate followed by 100 µl of cells (~$1×10^7$ cell per well). Cell mixtures were incubated for 0, 1, 2, 5 or 10 minutes before the entire contents of each well was applied to GF/C glass micro-filters (Whatman, Florham Park, N.J.) under vacuum. Each filter was washed 5 times with NCS medium before being transferred to vials containing 1.5 mL of scintillation fluid. Counts per minute were measured for each sample using a Tri-Carb 2900TR scintillation counter (PerkinElmer, Waltham, Mass.) and the total pmol of sugar incorporated into cells was determined by comparison to a standard curve generated with [$^3$H]GlcNAc.

Figure 8:
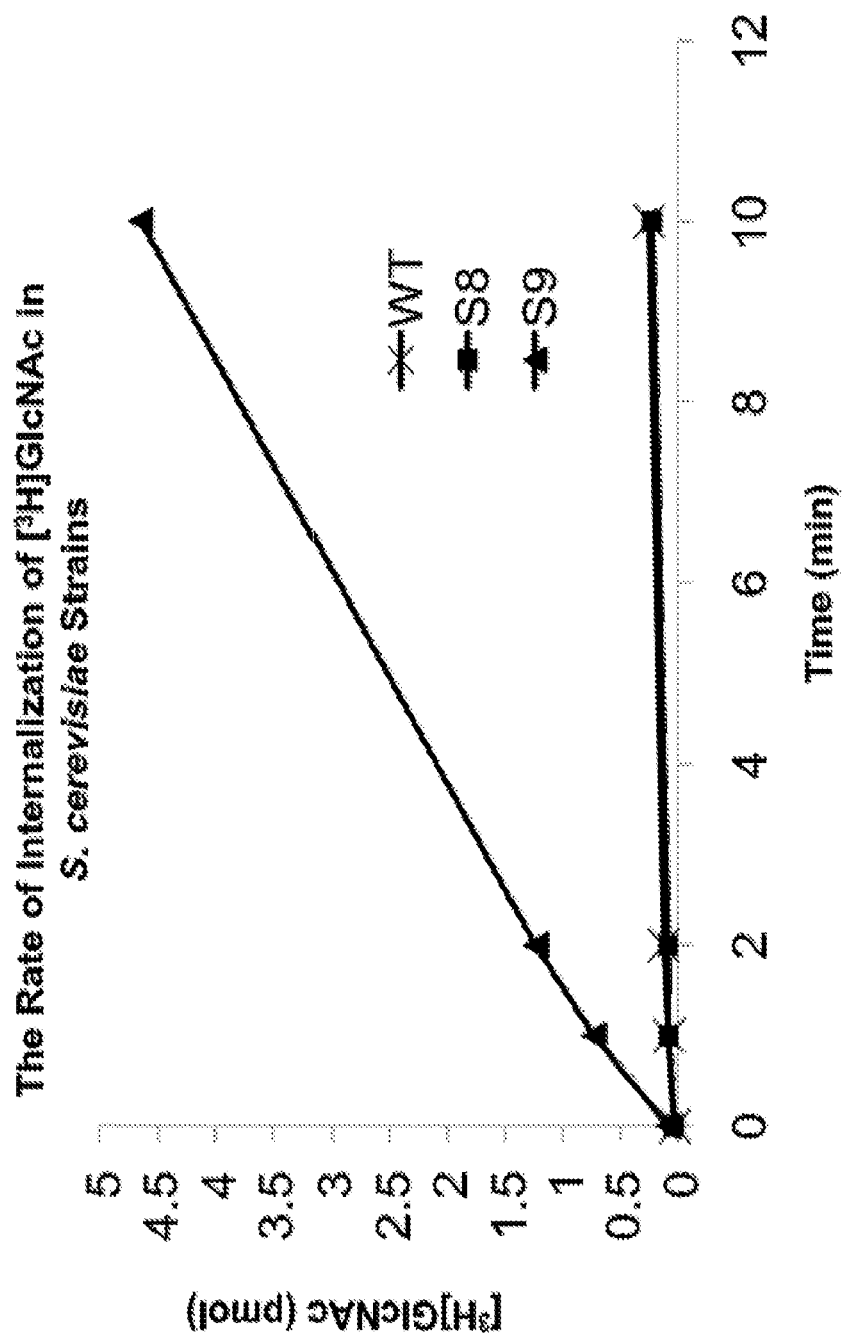
FIG. 8 depicts the rate of transport of [$^3$H]GlcNAc into modified S. cerevisiae cells. A sample population of $10^7$ cells of the parental strain (WT) and $10^7$ cells of strain modified S. cerevisiae (S8) each internalized GlcNAc at a rate of 0.016 pmol min$^{-1}$. Modified S. cerevisiae (S9) which is similar to strain S8 but also co-expresses the GlcNAc-specific transporter CaNgt1p internalizes [$^3$H]GlcNAc faster at 0.445 pmol min$^{-1}$ for a sample population of $10^7$ cells.

Expression of CaNgt1p increased the rate at which [$^3$H] GlcNAc was internalized by *S. cerevisiae* cells from 0.016 (for control strain strains S1 and strain S8) to 0.445 pmol GlcNAc $min^{-1}$ for strain S9 (FIG. 8).

Example 5

Growth Profiles of Engineered *S. cerevisiae* Strains

The growth of strains S1 (WT), S8 and S9 were compared by culturing each strain in 40 mL synthetic medium containing 20 µg $mL^{-1}$ methionine and either 100 mM glucose or 100 mM GlcNAc in 250 mL flasks. Cultures were grown at 30° C. for 120 hours with shaking at 280 r.p.m. At various times, a small aliquot of cells was removed from each culture and cell density was determined by measuring light absorbance at 600 nm. Measurements were plotted versus time to generate a growth profile for each culture (FIG. 7). Parental S1 cells grew in glucose-containing medium, but not GlcNAc. There was a slight reduction in the rate of growth of both S8 and S9 GlcNAc-medium compared to S1 in glucose-medium. However, S8 and S9 each grew to the same level of culture saturation in both glucose- and GlcNAc-containing medium as S1 grown in glucose.

Example 6

Fermentation of GlcNAc to Ethanol by Engineered S. cerevisiae Strains

The parent strain S. cerevisiae BY4734 and GlcNAc-assimilating strains S8 and S9 were cultured in triplicate in liquid medium for production of ethanol. Cultures of each strain were grown overnight in liquid YPGal culture medium (per liter: 10 g Yeast Extract, 20 g Bacto™ peptone (Becton Dickinson Difco Laboratories, Detroit, Mich.), 20 g D-galactose) with shaking at 30° C. Cells in overnight cultures were pelleted by centrifugation for 10 min at 5000 r.p.m. Cell pellets were washed once with 10 mL sterile deionized water and resuspended in 10 mL sterile deionized water. The cell density of the suspension was measured by light absorbance at 595 nm ($A_{595}$). Cells were diluted to a final $A_{595}$ of ~0.05 in 70 mL Difco™ yeast nitrogen base medium (Beckton, Dickinson & Co, Sparks, Md.) supplemented with the necessary amino acids and nucleotides needed to complement strain auxotrophies and 100 mM of either glucose or GlcNAc as a sole carbon source. To achieve oxygen limitation during culturing, the cultures (70 mL) were grown in loosely capped 125 mL flasks leaving little space for air above the culture. Cells were grown for 49 hours at 30° C. with only gentle shaking.

Ethanol in spent culture medium was measured enzymatically in a colorimetric alcohol oxidase assay using a commercial kit (Biovision Research Products, Mountain View, Calif.). The spent medium from each culture was cleared of cells by centrifugation for 10 min at 5000 r.p.m. Ten microliters of cleared medium from each culture was diluted with 190 µL deionized water, after which 5 µL of diluted sample was added to 45 µL of the kit's proprietary assay buffer. Reactions were performed according to the manufacturer's instructions. Briefly, samples diluted in assay buffer (50 µL) were added to 50 µL of the kit's reaction mix (45 µL 1× assay buffer, 2 µL ethanol probe, 2 µL ethanol enzyme mix) and incubated in the dark at room temperature for 60 min. The absorbance of each reaction at 570 nm was measured and ethanol in each sample was quantified by comparison to a standard curve generated using ethanol standards provided with the kit per the manufacturer's protocol.

Both engineered strains S8 and S9 were capable of fermenting GlcNAc and glucose to ethanol under oxygen limiting conditions (FIG. 9). Both strains produced similar amounts of ethanol when grown on glucose and on GlcNAc.

---

What is claimed is:

1. A composition, comprising: a genetically engineered *Saccharomyces* cell containing heterologous DNA encoding an N-acetyl glucosamine (GlcNAc) kinase, an N-acetylglucosamine-6-phosphate deacetylase and a glucosamine-6-phosphate deaminase.

2. The composition according to claim 1, capable of utilizing GlcNAc as a nutrient carbon source for conversion to a biofuel.

3. The composition according to claim 1, capable of utilizing GlcNAc as a nutrient carbon source for conversion to ethanol.

4. The composition according to claim 1, wherein the N-acetyl glucosamine kinase, the N-acetylglucosamine-6-phosphate deacetylase and the glucosamine-6-phosphate deaminase are expressed from DNA obtainable from *Candida albicans*.

5. A method for making a biofuel, comprising:
modifying a *Saccharomyces* yeast cell that naturally does not metabolize GlcNAc by introducing heterologous DNA into the *Saccharomyces* yeast-cell, the heterologous DNA encoding an N-acetyl glucosamine (GlcNAc) kinase, an N-acetylglucosamine-6-phosphate deacetylase and a glucosamine-6-phosphate deaminase;
providing GlcNAc as a source of nutrient carbon to the modified *Saccharomyces* yeast cell; and
permitting metabolic conversion of the GlcNAc to the biofuel by propagation of the modified *Saccharomyces* yeast cell.

6. The method according to claim 5, wherein the step of modifying the *Saccharomyces* yeast cell further comprises forming the heterologous DNA by assembling gene expression cassettes using PCR.

7. The method according to claim 6, further comprising obtaining the genes for the gene expression cassettes from *Candida albicans*.

8. The method according to claim 5, wherein the heterologous DNA encodes at least one protein selected from the group consisting of: N-acetyl glucosamine (GlcNAc)-specific transporter (CaNgt1p), GlcNAc kinase (CaNag5p), GlcNAc-6-phosphate deacetylase (CaNag2p) and glucosamine-6-phosphate deaminase (CaNag1p).

9. The method according to claim 5, wherein the biofuel is ethanol.

10. The method according to claim 5, wherein step (d) further comprises propagating the modified *Saccharomyces* yeast cell in aerobic conditions, oxygen-limited conditions or anaerobic conditions.

11. The method according to claim 5, wherein step (d) further comprises propagating the modified *Saccharomyces* yeast cell in a mixture of anaerobic and aerobic conditions during different phases of fermentation.

12. The method according to claim 5, wherein the step of propagating the *Saccharomyces* yeast cell further comprises providing at least one other sugar in addition to GlcNAc.

13. The method according to claim 12, wherein the at least one other sugar is selected from the group consisting of glucose, mannose, galactose, arabinose, fructose, xylose and glucosamine.

14. The method according to claim 5, wherein the heterologous DNA is from a second yeast cell capable of metabolizing GlcNAc.

15. The method according to claim 14, wherein the second yeast cell is *Candida albicans*.

16. The method according to claim 5, wherein the GlcNAc is derived from chitin.

* * * * *

SEQUENCE LISTING

```
<160> NUMBER OF SEQ ID NOS: 13

<210> SEQ ID NO 1
<211> LENGTH: 59
<212> TYPE: DNA
<213> ORGANISM: artificial
<220> FEATURE:
<223> OTHER INFORMATION: primer

<400> SEQUENCE: 1
ttatctactt tttacaacaa atataaaaca atgactgaga ctacattagt gggttgcgt        59

<210> SEQ ID NO 2
<211> LENGTH: 36
<212> TYPE: DNA
<213> ORGANISM: artificial
<220> FEATURE:
<223> OTHER INFORMATION: primer

<400> SEQUENCE: 2
cgcggatccc tacttatgat aggcagcacc tatggc                                 36

<210> SEQ ID NO 3
<211> LENGTH: 60
<212> TYPE: DNA
<213> ORGANISM: artificial
<220> FEATURE:
<223> OTHER INFORMATION: primer

<400> SEQUENCE: 3
ttatctactt tttacaacaa atataaaaca atgtcattta ctagattcac aaactgtcat       60

<210> SEQ ID NO 4
<211> LENGTH: 33
<212> TYPE: DNA
<213> ORGANISM: artificial
<220> FEATURE:
<223> OTHER INFORMATION: primer

<400> SEQUENCE: 4
```
cgcggatccc tataaaacag cagttaattt atc                                      33

<210> SEQ ID NO 5
<211> LENGTH: 60
<212> TYPE: DNA
<213> ORGANISM: artificial
<220> FEATURE:
<223> OTHER INFORMATION: primer

<400> SEQUENCE: 5
ttatctactt tttacaacaa atataaaaca atgagacaag ctatattttc caaccctaac          60

<210> SEQ ID NO 6
<211> LENGTH: 36
<212> TYPE: DNA
<213> ORGANISM: artificial
<220> FEATURE:
<223> OTHER INFORMATION: primer

<400> SEQUENCE: 6
cgcggatccc tacaactttg actttaatcc agcggc                                   36

<210> SEQ ID NO 7
<211> LENGTH: 60
<212> TYPE: DNA
<213> ORGANISM: artificial
<220> FEATURE:
<223> OTHER INFORMATION: primer

<400> SEQUENCE: 7
ttatctactt tttacaacaa atataaaaca atggagaaag atcaaactaa aatggatatt         60

<210> SEQ ID NO 8
<211> LENGTH: 33
<212> TYPE: DNA
<213> ORGANISM: artificial
<220> FEATURE:
<223> OTHER INFORMATION: primer

<400> SEQUENCE: 8
cgcggatcct tactcaatat gtactgttgt tga                                      33

<210> SEQ ID NO 9
<211> LENGTH: 40
<212> TYPE: DNA
<213> ORGANISM: artificial
<220> FEATURE:
<223> OTHER INFORMATION: primer

<400> SEQUENCE: 9
ataagaatgc ggcggcgtgg cctcttatcg agaaagaaat                               40

<210> SEQ ID NO 10
<211> LENGTH: 60
<212> TYPE: DNA
<213> ORGANISM: artificial
<220> FEATURE:
<223> OTHER INFORMATION: primer

<400> SEQUENCE: 10
acgcaaccca ctaatgctag tctcagtcat tgttttatat tgttgtaaa aagtagataa          60

<210> SEQ ID NO 11
<211> LENGTH: 60
<212> TYPE: DNA
<213> ORGANISM: artificial

-continued

```
<220> FEATURE:
<223> OTHER INFORMATION: primer

<400> SEQUENCE: 11
atgacagttt gtgaatctag taaatgacat tgttttatat ttgttgtaaa aagtagataa      60

<210> SEQ ID NO 12
<211> LENGTH: 60
<212> TYPE: DNA
<213> ORGANISM: artificial
<220> FEATURE:
<223> OTHER INFORMATION: primer

<400> SEQUENCE: 12
gttagggttg gaaaatatag cttgtctcat tgttttatat ttgttgtaaa aagtagataa      60

<210> SEQ ID NO 13
<211> LENGTH: 60
<212> TYPE: DNA
<213> ORGANISM: artificial
<220> FEATURE:
<223> OTHER INFORMATION: primer

<400> SEQUENCE: 13
aatatccatt ttagtttgat ctttctccat tgttttatat ttgttgtaaa aagtagataa      60
```